United States Patent
Marincek et al.

(10) Patent No.: US 10,559,938 B2
(45) Date of Patent: Feb. 11, 2020

(54) LASER SYSTEM FOR TISSUE ABLATION

(71) Applicant: Fotona d.d., Ljubljana (SI)

(72) Inventors: Marko Marincek, Ljubljana (SI); Janko Nendl, Ljubljana (SI); Matjaz Mocnik, Ljubljana (SI); Lukac Matjaz, Ljubljana (SI)

(73) Assignee: Fotona d.o.o., Ljubljana (SI)

( * ) Notice: Subject to any disclaimer, the term of this patent is extended or adjusted under 35 U.S.C. 154(b) by 708 days.

(21) Appl. No.: 14/948,454

(22) Filed: Nov. 23, 2015

(65) Prior Publication Data

US 2016/0149372 A1    May 26, 2016

(30) Foreign Application Priority Data

Nov. 24, 2014    (EP) .................... 14194452

(51) Int. Cl.
*A61B 18/20* (2006.01)
*H01S 3/11* (2006.01)
(Continued)

(52) U.S. Cl.
CPC .............. *H01S 3/11* (2013.01); *A61B 18/20* (2013.01); *H01S 3/092* (2013.01);
(Continued)

(58) Field of Classification Search
None
See application file for complete search history.

(56) References Cited

U.S. PATENT DOCUMENTS

2006/0054602 A1   3/2006  Kodokoro et al.
2008/0285600 A1*  11/2008 Marincek ............... A61B 18/20
                                                        372/10

FOREIGN PATENT DOCUMENTS

WO    03/072189 A2   9/2003
WO    2005/016586 A2  2/2005
(Continued)

OTHER PUBLICATIONS

Extended European Search Report for corresponding European Patent Application No. 14194452.0 dated May 12, 2015.

*Primary Examiner* — Michael W Kahelin
*Assistant Examiner* — Sana Sahand
(74) *Attorney, Agent, or Firm* — Renner, Otto, Boisselle & Sklar, LLP (57) ABSTRACT

A Laser system is disclosed which comprises a pump, wherein the laser system is adapted to be operated in pulsed operation so that at least one individual pulse of a temporally limited pulse duration ($T_0$) is generated, wherein the pulse ablates a material such that a debris cloud forms above the ablated material. Further, the pump power of the pump is modulated in such a way that the following three conditions are fulfilled: (1) the intensity of the pulse oscillates between maximum values and minimum values during the pulse duration, wherein the laser pulse comprises a plurality of intensity maxima $I_{max}$ which occur at times $\{T_i, i=1, \ldots N\}$; and a plurality of intensity minima $I_{min}$ which occur at times $\{t_k, k=1, \ldots (N-1)\}$, wherein the intensity does not vanish at the intensity minima; (2) the intensity oscillations of the laser pulse induce oscillations of the size of the debris cloud so that, during the pulse duration ($T_0$), there are at least two maxima of the size of the debris cloud which occur at times $\{\tau_j, j=1, \ldots M\}$ and which are located in between two intensity maxima of the laser pulse; and (3) at least 70 percent of the maxima of the size of the debris cloud occur near an intensity minimum of the pulse such that, for at least 70 percent of the maxima of the size of the debris cloud, the intensity of the pulse $I(\tau_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the (Continued)

debris cloud at time $\tau_j$ and $I_{max}(T_i)$ is the intensity maximum of the pulse which is closest to the maximum of the size of the debris cloud at time $\tau_j$.

15 Claims, 6 Drawing Sheets

(51) Int. Cl.
*H01S 3/092* (2006.01)
*A61B 18/00* (2006.01)
*A61B 17/00* (2006.01)

(52) U.S. Cl.
CPC ............... *A61B 2017/00185* (2013.01); *A61B 2018/00029* (2013.01); *A61B 2018/00577* (2013.01); *A61B 2018/00642* (2013.01)

(56) References Cited

FOREIGN PATENT DOCUMENTS

| WO | 2011/123449 A2 | 10/2011 |
| WO | 2012/135036 A2 | 10/2012 |

* cited by examiner

LASER SYSTEM FOR TISSUE ABLATION

This application claims priority of European Application No. 14194452.0 filed Nov. 24, 2014, which is hereby incorporated herein by reference.

TECHNICAL BACKGROUND

In the field of medicine, dentistry or the like, pulsed lasers are used for the removal of hard and soft body tissues such as dental enamel, dentine, bone material, skin and mucosa. The material removal in tissue ablation is based on a pronounced absorption of the temporally limited laser pulse in the ablated tissue. The laser absorption leads to local heating with sudden evaporation that causes material removal.

Depending on the laser intensity I (optical power per unit area) two distinct ablation regimes can be encountered in pulsed laser ablation. At low intensities, the speed of ablation is lower than the speed at which the laser-generated heat diffuses away from the ablated surface area deeper into the tissue. In this regime, the thermally influenced layer of tissue that is not ablated by the end of the laser pulse is relatively thick. For most medical procedures this "hot" regime is not desirable, since it may result in thermal tissue necrosis.

At high laser intensities, however, the ablation front progresses into the tissue faster than heat diffusion. In this "cold" regime, most of the preheated tissue is eventually ablated by the end of the pulse, and the amount of remaining heat which is deposited within the tissue is low.

It is to be appreciated that for the same laser pulse energy, long pulses have lower intensity and therefore ablate in the "hot" regime, while short pulses have high intensity and ablate in the clinically desirable "cold" regime.

The sudden material evaporation generated by individual laser pulses also results in a cloud of removed gases, liquids and solid particles (further on referred to also as "debris", "debris cloud", "debris particles" or "cloud particles") above the treated location, wherein the cloud begins to form immediately after the onset of each laser pulse and interacts with the impinging light until the end of the laser pulse. When the individual pulse impinges on the aforementioned debris cloud, the cloud particles get rapidly heated up to very high temperatures, sometimes leading to plasma formation within the surrounding gases and air. As a result, pulsed laser ablation is typically accompanied by undesirable high intensity visible and UV light being emitted from the debris cloud area. Additionally, the rapid absorption of the laser light in the debris cloud enhances the burning smell and popping sound that normally accompany pulsed laser ablation. Further, as the laser-heated debris cloud falls back onto the tissue surface, it contributes to the heating of the tissue. All these accompanying effects are unpleasant and potentially unsafe for the practitioner and the patient.

The size of the debris cloud and hence the above-described undesirable effects can be reduced to a certain degree by delivering laser energy with pulses of longer duration. Here, "size of the debris cloud" means the amount of debris particles which the laser beam has to cross, in order to reach the treated region of the tissue (the amount of debris particles can be measured in mole or gram). With laser pulses of longer duration, both the size of the debris cloud and the intensity of the impinging laser light are lower, and consequently the undesirable effects of the interaction of the laser light with the debris cloud are reduced.

In conclusion, the shorter and more intense the pulses are, the less undesirable heat remains deposited within the treated tissue, after the pulse has ended. Typically, pulses shorter than 350 microseconds are used to achieve ablation in the cold regime. On the other hand, the undesirable effects of the interaction of the laser light with the debris cloud are much less pronounced at longer pulse durations 350 microseconds) and lower pulse intensities.

The invention has the object to develop a laser system of the aforementioned kind which operates at longer pulse durations 350 microseconds) for which the above-described undesirable effects resulting from the interaction of the pulsed laser light with the debris cloud are considerably reduced, without significantly increasing the amount of heat that remains deposited within the treated tissue.

SUMMARY OF THE INVENTION

This object is solved by a laser system having the features of claim 1.

According to one aspect, the laser system of the present invention comprises a pump, wherein the laser system is operated in pulsed operation so that at least one individual pulse of a temporally limited pulse duration ($T_0$) is generated, wherein the pulse ablates a material such that a debris cloud forms above the ablated material; and wherein the pump power of the pump is modulated in such a way that the following three conditions hold:

(1) the intensity of the pulse oscillates between maximum values and minimum values during the pulse duration, wherein the laser pulse comprises a plurality of intensity maxima $I_{max}$ which occur at times $\{T_i, i=1, \ldots N\}$; and a plurality of intensity minima $I_{min}$ which occur at times $\{t_k, k=1, \ldots (N-1)\}$ (wherein the intensity does not vanish at the intensity minima); and (2) the intensity oscillations of the laser pulse induce oscillations of the size of the debris cloud so that, during the pulse duration ($T_0$), there are at least two maxima of the size of the debris cloud which occur at times $\{\tau_j, j=1, \ldots M\}$ and which are located in between two intensity maxima of the laser pulse; and (3) at least 70 percent of the maxima of the size of the debris cloud occur near an intensity minimum of the pulse such that, for at least 70 percent of the maxima of the size of the debris cloud, the intensity of the pulse $I(t_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $t_j$ and $I_{max}(T_i)$ is the intensity maximum of the pulse which is closest to the maximum of the size of the debris cloud at time $\tau_j$ (i.e., $I_{min}(t_k)$ is the intensity minimum of the pulse for which, among all the intensity minima of the pulse, the corresponding time $t_k$ is closest to the time $\tau_j$. Analogously, $I_{max}(T_i)$ is the intensity maximum of the pulse for which, among all the intensity maxima of the pulse, the corresponding time $T_i$ is closest to the time $t_j$).

Preferably, it holds for at least 90 percent of the maxima of the size of the debris cloud that they occur near an intensity minimum of the pulse, i.e., for at least 90 percent of the maxima of the size of the debris cloud, the intensity of the pulse $I(\tau_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $t_j$ and $I_{max}(T_i)$ is the intensity maximum of the pulse which is closest to the maximum of the size of the debris cloud at time $\tau_j$.

Preferably, the intensity of the laser pulse $I(\tau_j)$ at the respective time of the maximum of the size of the debris cloud is smaller than $I_{min}(t_k)+0.35\times[I_{max}(T_i)-I_{min}(t_k)]$, more preferably smaller than $I_{min}(t_k)+0.2\times[I_{max}(T_i)-I_{min}(t_k)]$ and most preferably smaller than $I_{min}(t_k)+0.1\times[I_{max}(T_i)-I_{min}(t_k)]$.

According to another aspect, the laser system of the present invention comprises a pump, wherein the laser system is adapted to be operated in pulsed operation so that at least one individual pulse of a temporally limited pulse duration ($T_0$) is generated and wherein the pulse ablates a material such that a debris cloud forms above the ablated material, and wherein the pump power of the pump is modulated in such a way that the following three conditions hold:

(1) the intensity of the pulse oscillates between maximum values and minimum values during the pulse duration, wherein the laser pulse comprises a plurality of intensity maxima which occur at times $\{T_i, i=1, \ldots N\}$; and a plurality of intensity minima which occur at times $\{t_k, k=1, \ldots (N-1)\}$ (wherein the intensity does not vanish at the intensity minima);

(2) the intensity oscillations of the laser pulse induce oscillations of the size of the debris cloud so that, during the pulse duration ($T_0$), there are at least two maxima of the size of the debris cloud which occur at times $\{\tau_j, j=1, \ldots M\}$ and which are located in between two minima of the size of the debris cloud and in between two intensity maxima of the laser pulse; and (3) at least 50 percent of the intensity minima of the pulse occur near a maximum of the size of the debris cloud such that the time difference $|t_k-\tau_j|$ between the corresponding intensity minimum at time $t_k$ and the nearby maximum of the size of the debris cloud at time $\tau_j$ is smaller than $0.25\times|T_{i+1}-T_i|$, wherein $|T_{i+1}-T_i|$ is the time difference between those successive intensity maxima of the laser pulse which are located closest to the maximum of the size of the debris cloud at time $\tau_j$.

Preferably, it holds for 70 percent of the intensity minima of the pulse that the time difference $|t_k-\tau_j|$ between the intensity minimum at time $t_k$ and the nearby maximum of the size of the debris cloud at time $\tau_j$ is smaller than $0.25\times|T_{i+1}-T_i|$, wherein $|T_{i+1}"T_i|$ is the time difference between those successive intensity maxima of the laser pulse which are located closest to the maximum of the size of the debris cloud at time $\tau_j$. More preferably, it holds for 90 percent of the intensity minima of the pulse that the time difference $|t_k-\tau_j|$ between the intensity minimum at time $t_k$ and the nearby maximum of the size of the debris cloud at time $\tau_j$ is smaller than $0.25\times|T_{i+1}-T_i|$.

Preferably, it holds for those intensity minima of the pulse which occur near a maximum of the size of the debris cloud that the time difference $|t_k-\tau_j|$ between the intensity minimum at time $t_k$ and the nearby maximum of the size of the debris cloud at time $\tau_j$ is smaller than $0.10\times|T_{i+1}-T_i|$, wherein $|T_{i+1}-T_i|$ is the time difference between those successive intensity maxima of the laser pulse which are located closest to the maximum of the size of the debris cloud at time $\tau_j$.

The laser system according to the present invention solves the above-described conflict that short pulses minimize the heat deposition in the treated tissue, whereas long pulses are advantageous for the interaction of the laser pulse with the debris cloud. On the one hand, the modulated laser pulse which is generated by the laser system according to the present invention has a long overall duration $T_0$ which contains several spikes, wherein each spike has a short duration. This spiky shape of the laser pulse keeps the heat deposition to the treated tissue low, since, in between two maxima of the laser pulse, the intensity decreases to low values, thus allowing the treated tissue to cool down to lower temperatures. As a consequence, the heat flow into the tissue below the treated area and into the surroundings is stopped. On the other hand, the interaction between the laser pulse and the debris cloud is also reduced for the modulated laser pulses according to the present invention, since the laser intensity is close to minimal values at those times when the size of the debris cloud becomes maximal.

It is well known that pulsed lasers exhibit intensity spiking and "relaxation" intensity oscillations, especially at the beginning of a laser pulse when the laser operation abruptly exceeds the lasing threshold. These oscillations are relatively chaotic and are not synchronized with the debris cloud. Contrary to these "free" relaxation oscillations, the intensity oscillations according to the present invention are "pump-driven", meaning that the synchronized laser intensity oscillations are forced upon the laser by appropriately modulating the pumping power from the pumping means.

According to the invention, the laser output intensity is modulated such that the intensity peaks occur (approximately) at those times when the size of the debris cloud is low, and intensity minima occur (approximately) at those times when the size of the debris cloud is high.

According to another aspect of the invention, an intensity modulation ratio between an intensity maximum of the pulse with intensity $I_{max}(T_i)$ and a successive intensity minimum of the pulse with intensity $I_{min}(t_i)$ is defined as $R_i=(I_{max}(T_i)-I_{min}(t_i))/I_{max}(T_i)$. Then, for at least 70% of these $R_i$ values, $R_i$ shall be in the range of $\geq 0.20$, inclusive, and $\leq 0.95$, inclusive, preferably in the range of $\geq 0.4$, inclusive, and $\leq 0.90$, inclusive, and most preferably in the range of $\geq 0.7$, inclusive, and $\leq 0.85$, inclusive.

The lower limit for the intensity modulation ratio $R_i$ ensures that the intensity modulation is sufficiently high to reduce the effects of heat diffusion and of the debris-laser interaction (as explained above). And the upper limit for the intensity modulation ratio ensures that the laser never falls below the lasing threshold under varying ambient conditions.

According to another aspect of the present invention, during the development of the pulse, there are at least 3 and at most 20 intensity maxima, preferably four to twelve intensity maxima, and most preferably four to seven intensity maxima.

According to another aspect of the present invention, the pulse duration $T_0$ obeys the following relation $0.35\text{ ms}\leq T_0\leq 5\text{ ms}$, preferably $0.35\text{ ms}\leq T_0\leq 2\text{ ms}$ and most preferably approximately $0.75$ ms.

Maintaining these upper limits for the pulse duration and consequently for the number of maxima per pulse avoids overheating of the laser material and also of the treated tissue. And maintaining the aforementioned lower limit of the pulse duration $T_0$ avoids the high average intensities and large debris cloud densities that are characteristic for laser pulses of short duration.

According to another aspect of the present invention, the values of the intensity maxima $I_{max}$ of the laser pulse can vary within a range of 30%, more preferably within a range of 20%, and most preferably within a range of 10%. Likewise, the values of the intensity minima $I_{min}(t_i)$ vary within a range of 30%, more preferably within a range of 20%, and most preferably within a range of 10%.

According to another aspect of the present invention, the time difference $|T_i-T_{i+1}|$ between neighboring intensity maxima of the pulse is in the range of ≤80 μs and ≤250 μs.

According to another aspect of the present invention, the laser system comprises an Er:YAG or an Er,Cr:YSGG laser as laser source.

Choosing time differences in this numerical range is beneficial for the occurrence of oscillations for the size of the debris cloud.

According to the another aspect of the present invention, the laser system comprises a control unit, a pumping means, a laser source and a light delivery system, wherein the laser system is adapted to be operated to generate temporally limited individual output laser pulses with a temporal pulse length ($T_0$) and wherein the intensity within the individual pulse is modulated with a temporal modulation period ($T_M$) that is at least approximately synchronised with the rise and fall time of the size of the laser generated debris cloud.

The invention is also based on the following recognition:

When an ablative laser light pulse is directed onto the tissue, ablation of the tissue starts and leads to the emission of ablated particles above the tissue surface, so that a debris cloud forms. The debris cloud does not develop instantaneously. Particles begin to be emitted with some delay following the onset of a laser pulse and then they spread with a certain speed and with a certain solid angle above the ablated tissue surface. Therefore, at the beginning of the laser pulse, the impinging laser light must pass only through a low amount of debris before reaching the tissue. Only at later times during the development of a single laser pulse, when the debris cloud has already spread well above the tissue, the undesired effects of the interaction of the laser beam with the debris cloud become significant. The rise time, $t_R$ which is defined as the time period between the onset of a laser pulse and the time when the interaction of the debris cloud with the laser light becomes maximal is typically within a range of including 30 microseconds to including 100 microseconds, depending on the intensity of the laser light and the type of ablated tissue.

The debris cloud has also a decay time $t_d$ which defined as the time required for the debris cloud to settle down after the end of a laser pulse. The measured decay time is typically within a range of including 50 microseconds to including 150 microseconds, depending on the intensity and energy of the laser pulse and the type of ablated tissue.

DETAILED DESCRIPTION OF PREFERRED EMBODIMENTS

Some of the embodiments of the invention will be explained in the following with the aid of the drawings in more detail. It is shown in.

Figure 1:
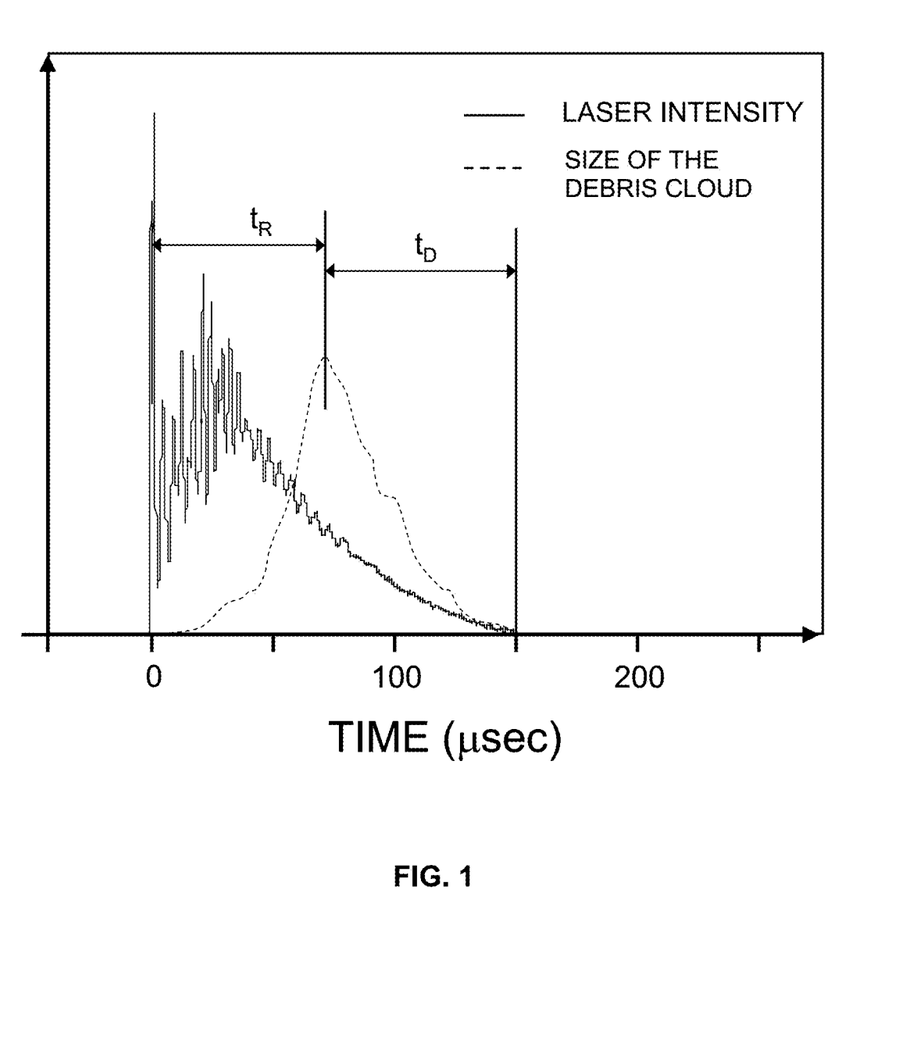
FIG. 1 a diagrammatic illustration of the temporal laser intensity and the temporal debris cloud development during the course of a laser pulse.

FIG. 1 shows a schematic illustration how a debris cloud is generated during the course of a prior art single laser pulse. In FIG. 1, the solid line curve represents the temporal shape of the laser pulse, and the dashed line curve represents the amount of light that gets scattered from the debris cloud which develops above the ablated surface and reaches a height of up to several millimeters above the surface. The intensity of scattered light thus represents a measure for the amount of debris particles which the laser beam has to cross, in order to reach the treated region of the tissue. Thus, the dashed line curve also represents the size of the debris cloud.

When the ablative laser light pulse is directed onto the organic tissue, ablation of the tissue starts and an ablation area is formed leading to the emission of ablated particles above the tissue surface, wherein the particles form a debris cloud. The debris cloud does not develop instantaneously, as can be seen in FIG. 1. Particles begin to be emitted with some delay following the onset of the laser pulse, after which they spread at a certain speed and with a certain solid angle above the ablated tissue surface. Therefore, at the beginning of the pulse, the amount of the emitted particles above the ablation area is low, while at a later time during the pulse development the particles extend well above the surface so that the amount of particles which the laser light must cross before reaching the tissue is high.

It can be seen from the scattered light curve that the debris cloud (FIG. 1) has a typical cloud rise time $t_R$, and a typical cloud decay time $t_D$. The cloud rise time, $t_R$, defined as the time period between the onset of a laser pulse and the time when the size of the debris cloud reaches its peak, is typically within a range of from 30 to 100 microseconds, depending on the intensity of the laser light and the type of ablated tissue. For the example shown in FIG. 1, the observed rise time is approximately 70 microseconds.

The debris cloud has also a decay time $t_d$ which is defined as the time required for the debris cloud to settle down from its peak size after the ending of a laser pulse. Typically, the decay time of the debris cloud is observed to be between 50 and 150 microseconds, depending on the laser pulse intensity and energy, and the tissue parameters. For the example shown in FIG. 1, the decay time of the debris cloud is approximately 80 microseconds.

Figure 2:
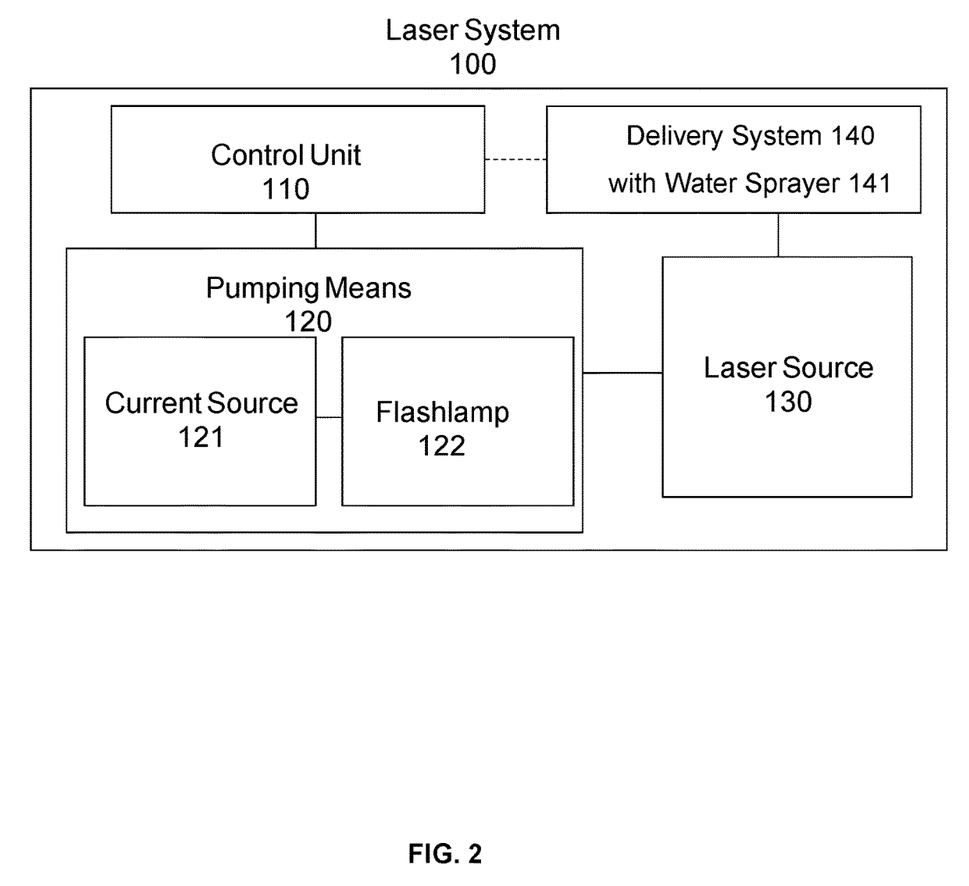
FIG. 2 a laser system according to the invention.

With reference now to FIG. 2, in various embodiments, a laser system 100 comprises a control unit 110, a pumping means 120, a laser source 130, and a light delivery system 140 wherein the laser system is adapted to be operated to generate temporally limited individual output laser pulses with an overall temporal pulse length $T_0$ and wherein the intensity within the individual pulse is modulated with a temporal modulation period.

In some of the preferred embodiments the laser source 130 operates in a wavelength range from above 1, 9 to 11 microns, such as solid-state Tm:YAG laser (wavelength of 2.0 microns), solid-state Ho:YAG laser (wavelength of 2.1 microns), solid-state Er:YAG laser (wavelength of 2.94 microns) and solid-state Er,Cr:YSGG laser (wavelength of 2.79 microns), or gas $CO_2$ laser (wavelength 9.3 to 10.6 microns) that is highly absorbed in water which is the major constituent of organic tissue. However, wavelengths below 1.9 microns may be used as well, particularly when the laser beam is focused to a sufficiently small spot in order to generate laser intensities above the tissue ablation threshold. Lasers with a wavelength below 1.9 microns may include a solid-state Nd:YAG laser (wavelength of 1.44, 1.32 or 1.06 microns), a solid-state Nd:YAP laser (wavelength of 1.34 or 1.08 microns) and solid-state KTP:YAG laser (wavelength of 5.3 microns) and various diode lasers (wavelengths in a range from 0.8 to 2.1 microns).

Figure 3:
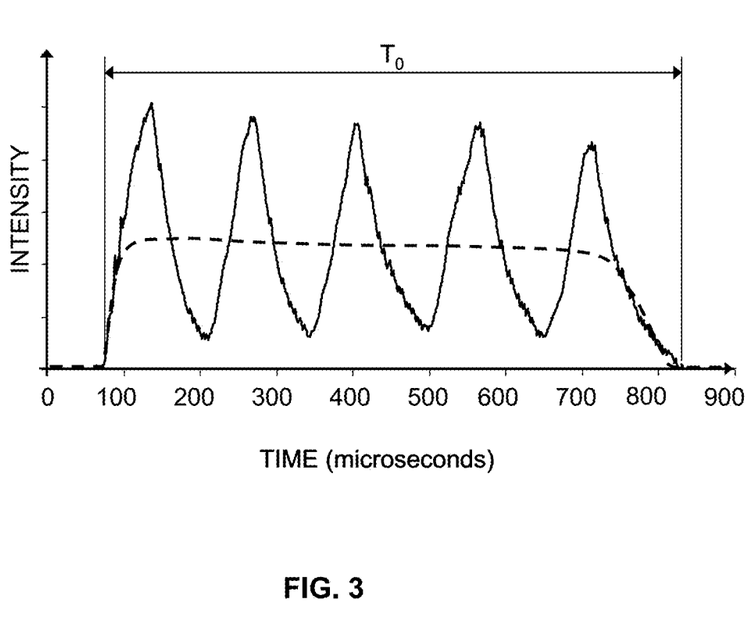
FIG. 3 a schematic illustration which shows the difference between the temporal development of the laser intensity according to the prior art and the temporal development of the laser intensity according to the present invention.

Referring now to FIG. 3, a modulated inventive laser pulse (represented by a solid line) with an overall pulse duration $T_0$ and energy $E_0$ can be seen. Such a modulated pulse is advantageously used in the present invention instead of a standard prior art laser pulse (represented by a dashed line) with the same overall pulse duration $T_0$ and energy $E_0$. The laser system may be operated such that these modulated individual pulses follow one another at a suitable temporal period $(T_P)$.

As can be also seen in FIG. 3, the modulated inventive laser pulse oscillates between maximum and minimum values, i.e. maxima and minima of the laser pulse intensity alternate, wherein the intensity maxima occur at times $\{T_i, i=1, \ldots N\}$ and the intensity minima occur at times $\{t_k, k=1, \ldots (N-1)\}$. Here and in the following, "maxima" and "minima" preferably refer to local maxima and local minima of the oscillation. The average temporal modulation period $T_M$ of the laser pulse can then be defined as the average time differences between successive pulse maxima, i.e. as the mean value for the values $|T_{i+1}-T_i|$.

The modulation of the intensity of the generated laser pulse is achieved by modulating the pump power of the laser pumping means 120 in an appropriate way. According to the invention, the laser pumping means 120 comprises at least a current source 121 wherein its output current is controlled by the control unit 140 in such a manner that a temporally limited output laser pulse with the desired intensity modulation is generated.

Figure 4:
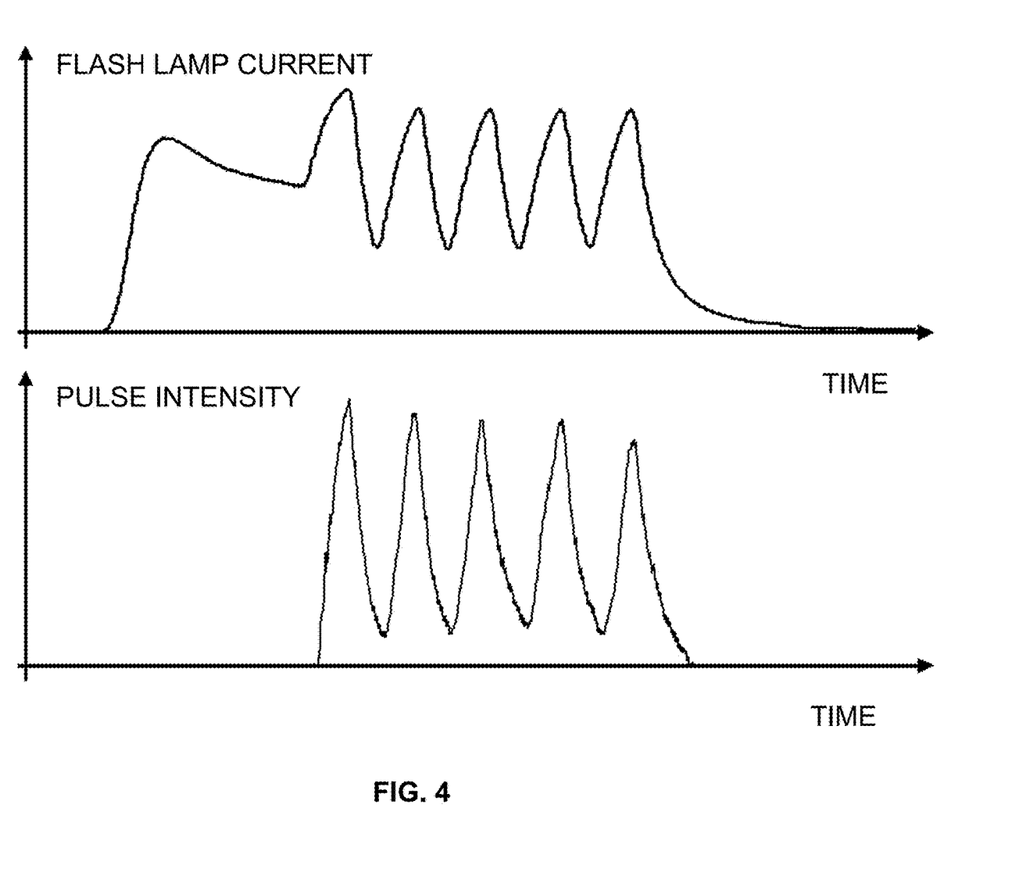
FIG. 4 an exemplary flash lamp current according to the present invention and the intensity of the laser pulse which is generated by the flash lamp current.

The top part of FIG. 4 shows an exemplary modulated flash lamp current, whereas the bottom part of FIG. 4 shows the pulse intensity of the laser pulse which is generated by that flash lamp current. One recognizes that the modulation periods of the flash lamp current and of the pulse intensity are approximately equal to each other.

In some of the embodiments, such as diode lasers or gas lasers, the current from the current source 121 flows directly through the laser material (a semiconductor or a gas) within the laser source 130, and pumps the laser source 130 to generate inventive output laser pulses. In yet other embodiments, the pumping means 120 consists additionally of an optical pump light source 122, such as a flash lamp or a diode, and the current from the current source 121 flows through the optical pump light source 122 that pumps the laser source 130, such as a solid-state laser, to generate inventive output laser pulses.

Flash lamps are commonly used to optically pump medical lasers. The conventional method of pulsing a flash lamp is to discharge a pulse forming network (PFN) through the flash lamp. A pulse forming network comprises capacitors to store electrical energy and inductances to limit the discharge current into the flash lamp load. The laser pulses resulting from a PFN pumped flash lamp are most commonly bell-shaped and of a fixed duration $T_0$. An example of a prior art PFN output laser pulse is shown in FIG. 1 (full line).

Another type of prior art pumping current sources for flash lamps in medical lasers is a variable square pulse (VSP) power supply. Here, a fraction of energy stored in a large capacitor bank is discharged through the flash lamp which provides nearly square shaped pump pulses that result also in nearly square shaped output laser pulses, the duration of which ($T_0$) can be conveniently controlled over a wide range of pulse duration by opening and closing a switching transistor, for example an IGBT transistor. A schematic example of a prior art VSP output laser pulse shape is shown in FIG. 3 (dashed line).

The above-described prior art pumping current sources for flash lamps in medical lasers are not well suited for creating inventive modulated laser pulses. Instead, in one preferred embodiment, a pulse width modulation (PWM) power supply may be used. The setup for modulating the pumping pulse intensity is described as follows. Electrical energy is stored in a large capacitor bank connected to the flash lamp via a fast switching IGBT transistor (Insulated Gate Bipolar Transistor). The flash lamp is first put into the low current conductive state controlled by a separate simmer power supply. The pumping pulse is initiated by switching the IGBT into the conductive state starting the electrical current to enter the flash lamp from the capacitor bank. By switching the IGBT with a train of control pulses the current through a flash lamp reaches a desired value depending on the electrical characteristics of the electronic circuit, switching frequency and pulse-width of the train of pulses. The effective current through the flash lamp can be thus controlled on-line with a processor by applying the pulse width modulation of the IGBT switching signal. FIG. 4 shows the modulated pump current according to the PWM method and the laser pulse which results from such modulation of the pump source and which can be advantageously used in the present invention.

Figure 5:
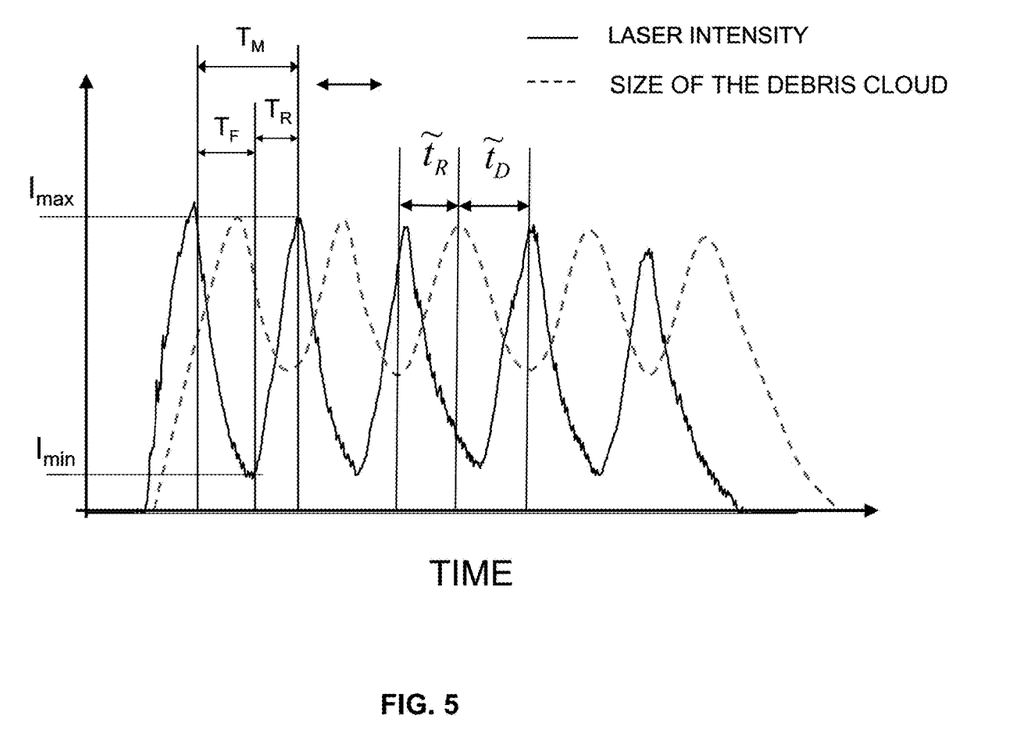
FIG. 5 in a diagrammatic illustration the temporal development of the pump-forced pulse intensity modulation according to the present invention.

FIG. 5 shows a schematic illustration of a particular embodiment of the invention. In FIG. 5, the full line curve represents the temporal shape of the laser pulse, and the dashed line curve represents the size of the debris cloud.

As can be seen in FIG. 5, the instantaneous intensity (I) of the laser pulse is modulated between minimum ($I_{min}$) and maximum ($I_{max}$) intensity values, with an intensity modulation factor $R:=(I_{max}-I_{min})/I_{max}$. These intensity values do not apply at the beginning and at the end of the pulse where the intensity starts and ends at zero value.

More generally, the values for the pulse intensity can vary at these maxima and minima. Then, a plurality of intensity modulation ratios can be defined as $R_i:=[I_{max}(T_i)-I_{min}(t_i)]/I_{max}(T_i)$, wherein $I_{max}(T_i)$ and $I_{min}(t_i)$ are the intensity values for the maximum at time $T_i$ and for the minimum at time $t_i$, respectively (in the above definition, $T_i<t_i$, and $t_i$ corresponds to the next (local) minimum which follows the maximum at $T_i$). As mentioned before, the time difference $|T_{i+1}-T_i|$ between two neighboring intensity maxima can vary to a certain degree between different intensity maxima of the pulse. The same holds for the intensity minima.

Further, the time differences $|T_{i+1}-T_i|$ between two neighboring intensity maxima, i.e. the oscillation period of the laser pulse, are chosen long enough such that, in between two successive pulse maxima, the debris cloud can decay to some extent. This means that the debris cloud, more precisely the size of the debris cloud, also oscillates during the pulse duration of the laser pulse (see the curve for the size of the debris cloud in FIG. 5). In particular, during the pulse duration ($T_0$), maxima of the size of the debris cloud and minima of the size of the debris cloud alternate.

In particular, since the debris cloud reacts to the laser pulse intensity with some delay, the modulation of the laser intensity can be done in such a way that the laser intensity is near a minimum when the size of the debris cloud is at a maximum value. In other words, the intensity minima of the laser pulse occur approximately at those times when the size of the debris cloud is maximal.

Further, it should be noted that the rise and decay times for the debris cloud which occur during the oscillatory behavior of the size of the debris cloud according to FIG. 5 are generally different from the rise and decay times $t_R$, $t_D$ which have been defined above in the context of FIG. 1, since, in FIG. 1, a laser pulse with a single maximum generates the debris cloud, whereas, in FIG. 5, a modulated laser pulse with several maxima is used. In particular, the size of the debris cloud does not decay to zero in FIG. 5, in contrast to the situation in FIG. 1. Accordingly, in FIG. 5, the cloud rise time $\tilde{t}_R$ for the debris cloud is defined as the time period in which the size of the debris cloud grows from a (non-vanishing) minimal value to a maximal value. Similarly, the cloud decay time $\tilde{t}_D$ is defined as the time period in which the size of the debris cloud decays from a maximal value to a (non-vanishing) minimal value. FIG. 5 illustrates the quantities $\tilde{t}_R$ and $\tilde{t}_D$.

In order that the approximate synchronisation between intensity minima of the laser pulse and maxima of the debris cloud can take place, the average modulation period $T_M$ of the laser pulse should be greater or equal to the sum of the cloud rise and decay times, i.e. $T_M \leq \tilde{t}_R + \tilde{t}_D$. The overall pulse duration ($T_0$) is shortest and consequently laser operation most efficient, if $T_M \approx \tilde{t}_R + \tilde{t}_D$. The (average) modulation spacing ($T_M$) is therefore preferably in the range of $\leq 80$ µs and $\geq 250$ µs.

The modulated laser pulse according to the present invention solves the above-described conflict that short pulses minimize the heat deposition in the treated tissue, whereas long pulses are advantageous for the interaction of the laser pulse with the debris cloud. The modulated laser pulse keeps the heat deposition to the treated tissue low, since, in between two maxima of the laser intensity, the laser intensity decreases to low values. This way, the treated tissue can cool down in between two pulse maxima so that the heat flow into the tissue below the treated area is also stopped. On the other hand, the interaction between the laser pulse and the debris cloud is also reduced for the modulated laser pulses according to the present invention, since the laser intensity is approximately minimal at those times when the size of the debris cloud becomes maximal.

From the viewpoint of heat deposition, it is advantageous to deliver the energy contained within a pulse in a strongly modulated manner, i.e. with a large intensity modulation ratio, in order to obtain high intensity maxima during which the ablation is faster than heat diffusion. The higher the intensity modulation ratio R, the less heat will remain deposited within the treated tissue at the end of the pulse.

Similarly, from the perspective of laser-debris interaction, the intensity modulation ratio R should be as close to R=1 as possible, since then the laser intensity is very small at those times when the size of the debris cloud becomes maximal. However, a modulation ratio of R=1 is not desirable as this would mean that at intensity minima the laser operation falls below the lasing threshold ($I_{min}=0$). A laser operated in such a regime would have to be re-pumped to above threshold following each intensity minimum, leading to lower overall laser system efficiency. Even more importantly, undesirable and uncontrolled large "relaxation" intensity oscillations would occur each time the laser would have to be re-pumped above the lasing threshold. This would lead to an unstable laser operation and a potential damage to the laser optics due to high intensity spikes, and would also interfere with the "pump-driven" intensity oscillations, potentially de-synchronizing the laser intensity modulation from the oscillations of the debris cloud. For this reason, according to our invention, the intensity modulation ratio R is in the range of $\geq 0.20$, inclusive, and $\leq 0.95$, inclusive, preferably in the range of $\geq 0.4$, inclusive, and $\leq 0.90$, inclusive, and expediently in the range of $\geq 0.7$, inclusive, and $\leq 0.85$, inclusive. The lower limit for the intensity modulation ratio ensures that the intensity modulation is sufficiently high to reduce the effects of heat diffusion and of the debris-laser interaction. And the upper limit for the intensity modulation ratio ensures that the laser operation never falls below the lasing threshold under varying ambient conditions.

In a preferred embodiment, a laser pulse comprises at least two intensity maxima ($I_{max}$). Preferably, a pulse has maximally 20 maxima, more preferably, however, three to twelve maxima and in particular five maxima. The duration of the pulse $T_0$ is preferably 0.35 ms $\leq T_0 \leq 5$ ms, advantageously 0.35 ms $\leq T_0 \leq 2$ ms and in particular approximately 0.75 ms. Maintaining the aforementioned upper limits for the pulse duration and consequently for the number of maxima per pulse avoids overheating of the laser material and also of the treated tissue. And maintaining the aforementioned lower limit of the pulse duration $T_0$ avoids the high average intensities and large debris cloud densities that are characteristic for laser pulses of short duration.

Figure 6:
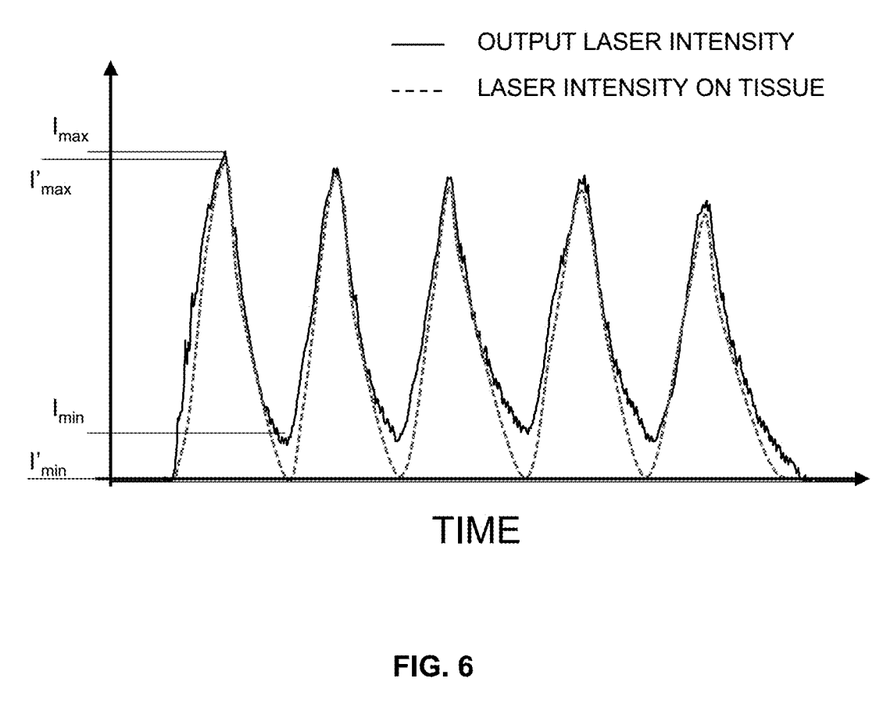
FIG. 6 in a diagrammatic illustration the temporal development of a pump-forced pulse intensity modulation according to the present invention, and a resulting pulse intensity on the tissue under water spray cooling conditions.

In one of further preferred embodiments the delivery system 140 may be equipped with a means to deliver water to the ablation area. The water may be delivered to the ablation area in the form of a water-air spray or in the form of a water jet. The water spray or water jet may intersect with the laser beam in the space directly above the ablation area, or it may be delivered to the ablation area from the side. What is important for this preferred embodiment is that in order to ablate the tissue the laser light must first pass through the water that is present in its path in the form of a water mist or a water jet above the ablation area, or as a water layer on the ablated surface. Now, it is well understood that when a laser light of intensity I having a wavelength which is in the range of 1.9 to 11 microns and which is absorbed by water impinges on any water in its path, some part of the laser light's energy is used up to evaporate the water, thus creating a vapor tunnel through which the laser light can proceed to the target. Since, in this process, some fraction of the energy is used up for evaporating the water, the initial output laser intensity I is correspondingly reduced to a smaller transmitted intensity I'. Since the energy required to create the vapor tunnel is fixed and does not depend on the laser intensity, the relative reduction in the intensity, (I−I')/I, is higher for smaller incoming intensities I and lower for larger incoming intensities I. The intensity minima ($I_{min}$) of the inventive modulated laser pulse are thus relatively more affected by the presence of water than the intensity maxima ($I_{max}$), as shown in FIG. 6. The resulting intensity modulation ratio $R'=(I'_{max}-I'_{min})/I'_{max}$ of the transmitted laser pulse is thus increased and the undesirable effects of the debris cloud are correspondingly reduced by the presence of water in the path of the laser pulse. In one of the embodiments, the incoming intensity minima $I_{min}$ may be chosen to be sufficiently low and the water delivery conditions may be selected such that the energy loss through water results in zero transmitted intensity ($I'_{min}=0$). Using this particular embodiment, the effects of the debris cloud can thus be further minimized without introducing threshold laser instabilities that would occur if the intensity minimum $I_{min}$ outputted from the laser was reduced to zero.

In one of the preferred embodiments, the laser is a flash lamp pumped solid state Er:YAG or Er,Cr:YSGG laser characterized in that the flash lamp is pumped by a PWM current source, and wherein the pulse duration ($T_0$) is in the range 0.5 ms $\leq T_0 \leq 9$ ms, and wherein there are four to six intensity maxima, and wherein the intensity modulation ratio R is in the range of ≤0.70, inclusive, and ≤0.95 inclusive, and wherein the temporal modulation spacing ($T_M$) between intensity maxima is in the range of ≤110 μs and ≤180 μs. In a further embodiment, the delivery system 140 is equipped with a means to deliver water to the vicinity of the ablation area in a form of a water spray or water jet; and wherein the laser pulse energy is partially absorbed in aforementioned water and wherein as a result the modulation ratio R' of the transmitted light is favorably increased.

For a better understanding of the present invention, the following embodiments are listed:

Embodiment 1

Laser system, comprising:
   a pump,
      wherein the laser system is adapted to be operated in pulsed operation so that at least one individual pulse of a temporally limited pulse duration ($T_0$) is generated,
      wherein the pulse ablates a material such that a debris cloud forms above the ablated material; and
      wherein the pump power of the pump is modulated in such a way that
         (1) the intensity of the pulse oscillates between maximum values and minimum values during the pulse duration, wherein the laser pulse comprises a plurality of intensity maxima $I_{max}$ which occur at times $\{T_i, i=1, \ldots N\}$; and a plurality of intensity minima $I_{min}$ which occur at times $\{t_k, k=1, \ldots (N-1)\}$, wherein the intensity does not vanish at the intensity minima; and
         (2) the intensity oscillations of the laser pulse induce oscillations of the size of the debris cloud so that, during the pulse duration ($T_0$), there are at least two maxima of the size of the debris cloud which occur at times $\{\tau_j, j=1, \ldots M\}$ and which are located in between two intensity maxima of the laser pulse; and
         (3) at least 70 percent of the maxima of the size of the debris cloud occur near an intensity minimum of the pulse such that, for at least 70 percent of the maxima of the size of the debris cloud, the intensity of the pulse $I(\tau_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

Embodiment 2

Laser system according to embodiment 1, wherein at least 90 percent of the maxima of the size of the debris cloud occur near an intensity minimum of the pulse such that, for at least 90 percent of the maxima of the size of the debris cloud, the intensity of the pulse $I(t_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $t_j$.

Embodiment 3

Laser system according to embodiment 1 or 2, wherein, for a maximum of the size of the debris cloud which occurs near an intensity minimum of the pulse, the intensity of the pulse $I(t_j)$ at the time of the maximum of the size of the debris cloud is smaller than $I_{min}(t_k)+0.35\times[I_{max}(T_i)-I_{min}(t_k)]$, wherein $I_{min}(t_k)$ is the intensity minimum of the pulse which is closest to the maximum of the size of the debris cloud at time $t_j$ and $I_{max}(T_i)$ is the intensity maximum of the pulse which is closest to the maximum of the size of the debris cloud at time $t_j$.

Embodiment 4

Laser system according to embodiment 3, wherein, for a maximum of the size of the debris cloud which occurs near an intensity minimum of the pulse, the intensity of the pulse $I(t_j)$ at the time of the maximum of the size of the debris cloud is smaller than $I_{min}(t_k)+0.2\times[I_{max}(T_i)-I_{min}(t_k)]$, wherein $I_{min}(t_k)$ is the intensity minimum of the pulse which is closest to the maximum of the size of the debris cloud at time $t_j$ and $I_{max}(T_i)$ is the intensity maximum of the pulse which is closest to the maximum of the size of the debris cloud at time $t_j$.

Embodiment 5

Laser system according to any of the preceding embodiments,
   wherein an intensity modulation ratio between an intensity maximum of the pulse with intensity $I_{max}(T_i)$ and a successive intensity minimum of the pulse with intensity $I_{min}(t_i)$ is defined as $R_i=(I_{max}(T_i)-I_{min}(t_i))/I_{max}(T_i)$, and wherein each intensity modulation ratio $R_i$ is in the range of ≥0.20, inclusive, and ≤0.95, inclusive, preferably in the range of ≤0.4, inclusive, and ≤0.90, inclusive, and most preferably in the range of ≥0.7, inclusive, and ≤0.85, inclusive.

Embodiment 6

Laser system according to any of the preceding embodiments,
   wherein the values of the intensity maxima $I_{max}(T_i)$ vary within a range of 30%, more preferably within a range of 20%, and most preferably within a range of 10%; and
   wherein the values of the intensity minima $I_{min}(t_i)$ vary within a range of 30%, more preferably within a range of 20%, and most preferably within a range of 10%.

Embodiment 7

Laser system according to any of the preceding embodiments,
   wherein the time difference $|T_i-T_{i+1}|$ between neighboring intensity maxima of the pulse is in the range of 80 μs and 250 μs.

Embodiment 8

Laser system according to any of the preceding embodiments, wherein, during the development of the pulse, there are at least 3 and at most 20 intensity maxima, preferably four to twelve intensity maxima, and most preferably four to seven intensity maxima.

Embodiment 9

Laser system according to any of the preceding embodiments, characterized in that the pulse duration ($T_0$) is ≤350 µs.

Embodiment 10

Laser system according to embodiment 9, characterized in that the pulse duration ($T_0$) is 0.35 ms≤$T_0$≤5 ms, preferably 0.35 ms≤$T_0$≤2 ms and most preferably approximately 0.75 ms.

Embodiment 11

Laser system according to any of the preceding embodiments, wherein the laser system is used for ablation of tissue.

Embodiment 12

Laser system according to any one of the preceding embodiments, characterized in that the laser is pumped by a flashlamp.

Embodiment 13

Laser system according to embodiment 12, characterized in that the flash lamp is pumped by a pulse width modulation (PWM) current source.

Embodiment 14

Laser system according to any one of the preceding embodiments,
wherein the laser wavelength lies in the range of 1.9 microns to 11 microns and is absorbed by water, and wherein the laser system further comprises a light delivery system (140) which comprises a means to deliver water to the vicinity of the ablation area in the form of a water spray or a water jet.

Embodiment 15

Laser system according to embodiment 14,
wherein the pulse energy of the pulse is partially absorbed in the water spray or the water jet so that the modulation ratios $R'_i$ of the transmitted light are increased.

What is claimed is:

1. A laser system for ablating a material such that a debris cloud of ablated particles of the material will form above the ablated material, comprising:
a pump,
a laser, and
a controller,
wherein the controller is configured to control the laser system for pulsed operation so that individual laser pulses of a temporally limited pulse duration are generated, and
wherein the controller is configured to modulate the pump such that
(1) the pulses have an intensity that oscillates between maximum values and minimum values during the pulse duration, wherein the laser pulse comprises a plurality of intensity maxima $I_{max}$ which occur at times $\{T_i, i=1, N\}$; and a plurality of intensity minima $I_{min}$ which occur at times $\{t_k, k=1, \ldots (N-1)\}$, wherein the intensity of the pulse does not vanish at the intensity minima, and wherein an average modulation period $T_M$ of the pulse is defined as a mean value of time differences $|T_{i+1}-T_i|$ between successive intensity maxima,
wherein the intensity oscillations of the laser pulse induce oscillations of a size of the debris cloud so that, during the pulse duration ($T_0$), there are at least two maxima of the size of the debris cloud which occur at times $\{\tau_j, j=1, M\}$ and which are located in between two intensity maxima of the laser pulse, and wherein an oscillation of the size of the debris cloud has a rise time $\tilde{t}_R$ and a decay time $\tilde{t}_D$; and
(2) the average modulation period $T_M$ of the pulse is greater or equal to a sum of a rise time $\tilde{t}_R$ and a decay time $\tilde{t}_D$ of an oscillation of the debris cloud so that at least 70 percent of the maxima of the size of the debris cloud occurs near an intensity minimum of the pulse such that, for at least 70 percent of the maxima of the size of the debris cloud, the intensity of the pulse $I(\tau_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

2. The laser system according to claim 1, wherein the controller is configured to control the laser system so that at least 90 percent of the maxima of the size of the debris cloud occur near an intensity minimum of the pulse such that, for at least 90 percent of the maxima of the size of the debris cloud, the intensity of the pulse $I(\tau_j)$ at the time of the maximum of the size of the debris cloud is smaller than $I_{min}(t_k)+0.5\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

3. The laser system according to claim 1, wherein the controller is configured to control the laser system so that, for a maximum of the size of the debris cloud which occurs near an intensity minimum of the pulse, the intensity of the pulse $I(\tau_j)$ at the time of the maximum of the size of the debris cloud is smaller than $I_{min}(t_k)+0.35\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

4. The laser system according to claim 3, wherein the controller is configured to control the laser system so that, for a maximum of the size of the debris cloud which occurs near an intensity minimum of the pulse, the intensity of the pulse $I(\tau_j)$ at the time of the maximum of the size of the debris cloud is smaller than $I_{min}(t_k)+0.2\times[I_{max}(T_i)-I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

5. The laser system according to claim 1,
wherein the controller is configured to control the laser system so that an intensity modulation ratio between an intensity maximum of the pulse with intensity $I_{max}(T_i)$ and a successive intensity minimum of the pulse with intensity $I_{min}(t_i)$ is defined as $$R_i = (I_{max}(T_i) - I_{min}(t_i))/I_{max}(T_i), \text{ and}$$

wherein each intensity modulation ratio $R_i$ is in the range of $\geq 0.20$, inclusive, and $\leq 0.95$, inclusive.

6. The laser system according to claim 1,
wherein the controller is configured to control the laser system so that the values of the intensity maxima $I_{max}(T_i)$ vary within a range of 30%; and
wherein the values of the intensity minima $I_{min}(t_i)$ vary within a range of 30%.

7. The laser system according to claim 1,
wherein the controller is configured to control the laser system so that the time difference $|T_i - T_{i+1}|$ between neighboring intensity maxima of the pulse is in the range of $\geq 80$ μs and $\leq 250$ μs.

8. The laser system according to claim 1, wherein the controller is configured to control the laser system so that, during the development of the pulse, there are at least 3 and at most 20 intensity maxima.

9. The laser system according to claim 1, wherein the controller is configured to control the laser system so that the pulse duration ($T_0$) is $\geq 350$ μs.

10. The laser system according to claim 9, wherein the controller is configured to control the laser system so that the pulse duration ($T_0$) is 0.35 ms $\leq T_0 \leq$ 5 ms.

11. The laser system according to claim 1, wherein the laser system is used for ablation of tissue.

12. The laser system according to claim 1, wherein the pump is a flashlamp.

13. The laser system according to claim 1,
wherein the laser wavelength lies in the range of 1.9 microns to 11 microns and is absorbed by water, and
wherein the laser system further comprises a light delivery system which comprises a water sprayer for delivering water to a vicinity of the ablation area in the form of a water spray or a water jet.

14. The laser system according to claim 13,
wherein the controller is configured to control the laser system so that the pulse energy of the pulse is partially absorbed in the water spray or the water jet so that the modulation ratios $R'_i$ of the transmitted light are increased.

15. A method for ablating a material by means of a pulsed laser, comprising the following steps:

generating at least one individual pulse of a temporally limited pulse duration ($T_0$), wherein the pulse ablates a material such that a debris cloud forms above the ablated material, wherein the debris cloud comprises ablated particles of the material; and modulating pump power of a pump of the laser in such a way that (1) the pulse has an intensity that oscillates between maximum values and minimum values during the pulse duration, wherein the pulse comprises a plurality of intensity maxima $I_{max}$ which occur at times $\{T_i, i=1, N\}$; and a plurality of intensity minima $I_{min}$ which occur at times $\{t_k, k=1, \ldots (N-1)\}$, wherein the intensity does not vanish at the intensity minima, and wherein an average modulation period $T_M$ of the pulse is defined as a mean value of the time differences $|T_{i+1} - T_i|$ between successive intensity maxima, wherein the intensity oscillations of the pulse induce oscillations of a size of the debris cloud so that, during the pulse duration ($T_0$), there are at least two maxima of the size of the debris cloud which occur at times $\{\tau_j, j=1, M\}$ and which are located in between two intensity maxima of the laser pulse, and wherein an oscillation of the size of the debris cloud has a rise time $\tilde{t}_R$ and a decay time $\tilde{t}_D$; and (2) an average modulation period $T_M$ of the pulse is greater or equal to a sum of the rise time $\tilde{t}_R$ and the decay time $\tilde{t}_D$ of an oscillation of the debris cloud so that at least 70 percent of the maxima of the size of the debris cloud occur near an intensity minimum of the pulse such that, for at least 70 percent of the maxima of the size of the debris cloud, the intensity of the pulse $I(\tau_j)$ at the time of the maximum of the size of the debris cloud is smaller than $I_{min}(t_k) + 0.5 \times [I_{max}(T_i) - I_{min}(t_k)]$, wherein $I_{min}(t_k)$ is the intensity minimum of the pulse which is closest to the maximum of the size of the debris cloud at time $\tau_j$ and $I_{max}(T_i)$ is the intensity maximum of the pulse which is closest to the maximum of the size of the debris cloud at time $\tau_j$.

* * * * *